US009880298B2

(12) United States Patent
Balakrishnan (10) Patent No.: US 9,880,298 B2
(45) Date of Patent: Jan. 30, 2018

(54) METHOD AND DEVICE FOR DETERMINING A POSITION OF POINT AND LINE SOURCES IN A POSITRON EMISSION TOMOGRAPHY (PET) APPARATUS

(71) Applicant: Toshiba Medical Systems Corporation, Otawara-shi (JP)

(72) Inventor: Karthikayan Balakrishnan, Vernon Hills, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 90 days.

(21) Appl. No.: 14/668,583

(22) Filed: Mar. 25, 2015

(65) Prior Publication Data

US 2016/0282486 A1 Sep. 29, 2016

(51) Int. Cl.
| | | |
|---|---|---|
| *G01T 1/164* | (2006.01) | |
| *G01T 1/29* | (2006.01) | |
| *A61B 5/00* | (2006.01) | |
| *G06T 11/00* | (2006.01) | |
| *G01T 5/02* | (2006.01) | |

(52) U.S. Cl.
CPC .......... *G01T 1/2985* (2013.01); *A61B 5/0033* (2013.01); *G01T 5/02* (2013.01); *G06T 11/005* (2013.01)

(58) Field of Classification Search
CPC ................................ G01T 5/02; A61B 5/0033
USPC ..................................................... 250/363.03
See application file for complete search history.

(56) References Cited

U.S. PATENT DOCUMENTS

| | | | | |
|---|---|---|---|---|
| 2007/0152162 A1* | 7/2007 | Griesmer | .............. | G01T 1/2985 250/363.09 |
| 2007/0290125 A1* | 12/2007 | Wang | .................... | G01T 1/1648 250/252.1 |
| 2011/0081068 A1* | 4/2011 | Brinks | .................. | G06T 11/005 382/132 |
| 2014/0286497 A1* | 9/2014 | Thyssen | ................. | H04R 3/005 381/66 |
| 2014/0376689 A1 | 12/2014 | Zou et al. | | |
| 2015/0355347 A1* | 12/2015 | Pratx | ...................... | A61B 6/037 600/426 |

FOREIGN PATENT DOCUMENTS

JP 2015-3026 A 1/2015

* cited by examiner

*Primary Examiner* — David Porta
*Assistant Examiner* — Abra Fein
(74) *Attorney, Agent, or Firm* — Oblon, McClelland, Maier & Neustadt, L.L.P.

(57) ABSTRACT

An apparatus and method for determining a position of a point source arranged in a Positron Emission Tomography (PET) scanner apparatus. The apparatus includes processing circuitry configured to obtain list-mode data generated from a PET scan of the point source, determine a plurality of lines-of-response (LORs) from the obtained list-mode data, determine intersecting pairs of LORs from the determined plurality of LORs, determine corresponding coordinates of intersection points of the determined intersecting pairs of LORs, and determine the position of the point source based on the determined coordinates of the intersections points.

12 Claims, 12 Drawing Sheets

METHOD AND DEVICE FOR DETERMINING A POSITION OF POINT AND LINE SOURCES IN A POSITRON EMISSION TOMOGRAPHY (PET) APPARATUS

BACKGROUND

Field

Embodiments described herein relate to determining a position of point and lines sources in a Positron Emission Tomography (PET) apparatus.

Background

The use of PET is growing in the field of medical imaging. In PET imaging, a radiopharmaceutical agent is introduced into an object to be imaged 15, shown in FIG. 1, via injection, inhalation, or ingestion. After administration of the radiopharmaceutical, the physical and bio-molecular properties of the agent will cause the agent to concentrate at specific locations in the human body (i.e., object 15). The actual spatial distribution of the agent, the intensity of the region of accumulation of the agent, and the kinetics of the process from administration to eventually elimination are all factors that may have clinical significance. During this process, a positron emitter attached to the radiopharmaceutical agent will emit positrons according to the physical properties of the isotope, such as half-life, branching ratio, etc.

Figure 1:
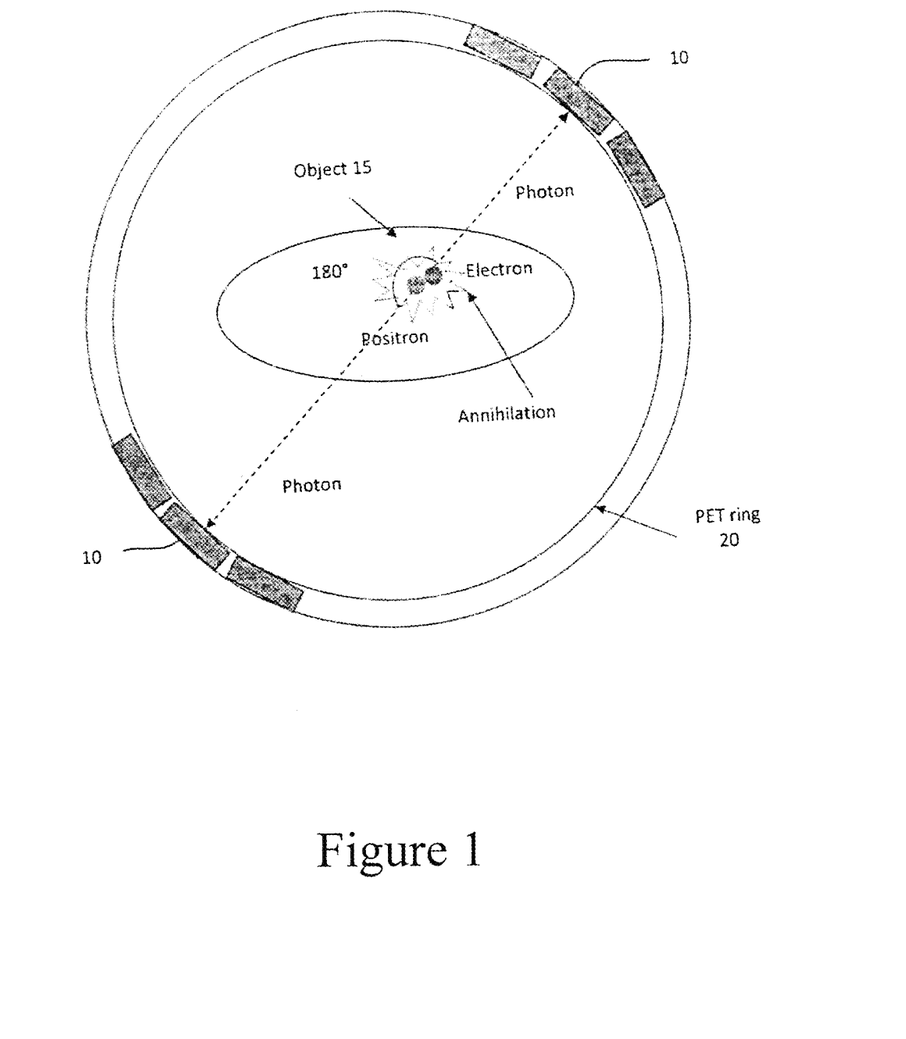
FIG. 1 shows a PET detector ring.

The radionuclide emits positrons, and when an emitted positron collides with an electron, an annihilation event occurs, wherein the positron and electron are destroyed. Most of the time, an annihilation event produces two gamma photons at 511 keV traveling at substantially 180 degrees apart which are detected by a pair of crystals. By drawing a line between centers of a pair of crystals 10, i.e., the line-of-response (LOR), or drawing a polyhedron formed by connecting corresponding corners of a pair of crystals 10, i.e., tube-of-response (TOR), one can retrieve the likely location of the original disintegration. While this process will only identify a line (or tube) of possible interaction, by accumulating a large number of those lines (or tubes), and through a tomographic reconstruction process, the original distribution can be estimated. In addition to the location of the two scintillation events, if accurate timing (within few hundred picoseconds) is available, a time-of-flight (TOF) calculation can add more information regarding the likely position of the event along the line (or tube).

The above-described detection process must be repeated for a large number of annihilation events. While each imaging case must be analyzed to determine how many counts (i.e., paired events) are required to support the imaging task, current practice dictates that a typical 100-cm long, FDG (fluoro-deoxyglucose) study will need to accumulate several hundred million counts. The time required to accumulate this number of counts is determined by the injected dose of the agent and the sensitivity and counting capacity of the scanner.

Briefly, the PET reconstruction process finds the amount and the location of isotopes (unknown) in the patient from the data recorded in the PET system (known). One of the basic questions in the PET reconstruction process is to find detection probability, which represents the probability of a photon emitted from a voxel that can be detected by a given pair of crystals 10.

For many calibration and analysis modes, a point source located at the iso-center of a PET scanner is required or a line source aligned to the scanner's cylindrical axis and centered radially is required. To determine the location of the source, conventional methods acquire data for a long period of time (ranging from tens of seconds to minutes) and perform image reconstruction. Thus, conventionally it takes a great deal of time to acquire and calculate the location of the point source or the line source.

BRIEF DESCRIPTION OF THE DRAWINGS

The disclosure will be better understood from reading the description which follows and from examining the accompanying figures. These figures are provided solely as non-limiting examples of the embodiments. In the drawings.

DETAILED DESCRIPTION

One embodiment is directed to an apparatus for determining a position of a point source arranged in a PET scanner apparatus. The apparatus including processing circuitry configured to obtain list-mode data generated from a PET scan of the point source, determine a plurality of LORs from the obtained list-mode data, determine intersecting pairs of LORs from the determined plurality of LORs, determine corresponding coordinates of intersection points of the determined intersecting pairs of LORs, and determine the position of the point source based on the determined coordinates of the intersections points.

One embodiment is directed to a method for determining a position of a point source arranged in a PET scanner apparatus. The method includes obtaining list-mode data generated from a PET scan of the point source; determining a plurality of LORs from the obtained list-mode data; determining intersecting pairs of LORs from the determined plurality of LORs; determining corresponding coordinates of intersection points of the determined intersecting pairs of LORs; and determining the position of the point source based on the determined coordinates of the intersection points.

On embodiment is directed to an apparatus for determining a position of a line source arranged in a PET scanner apparatus. The apparatus includes processing circuitry configured to obtain list-mode data generated from a PET scan of the line source, determine a plurality of LORs from the obtained list-mode data, determine intersecting pairs of LORs from the determined plurality of LORs, determine corresponding coordinates of points of intersections for the determined intersecting pairs of LORs, and determine the position of the line source by fitting the points of intersections for the intersecting pairs of LORs to a line and determining tilt of the line.

As noted above, for many calibration and analysis modes, a point source located at the iso-center of a PET scanner is required or a line source aligned to the scanner's cylindrical axis and centered radially is required. Embodiments discussed herein allow a user to check if the source is aligned in a very fast manner by accurately and quickly determining the location of the source.

In one embodiment, the point source is placed substantially at the scanner iso-center. The point source can be placed at the iso-center by simply "eye balling," which allows the point source to be placed within centimeters of the scanner iso-center. The PET scanner then acquires paired list-mode data for a very short duration. In one embodiment, this duration is less than a second. In one embodiment, acquisition time ranges are 0.5 seconds for point sources with activities in the milli-Curie range.

Figure 2:
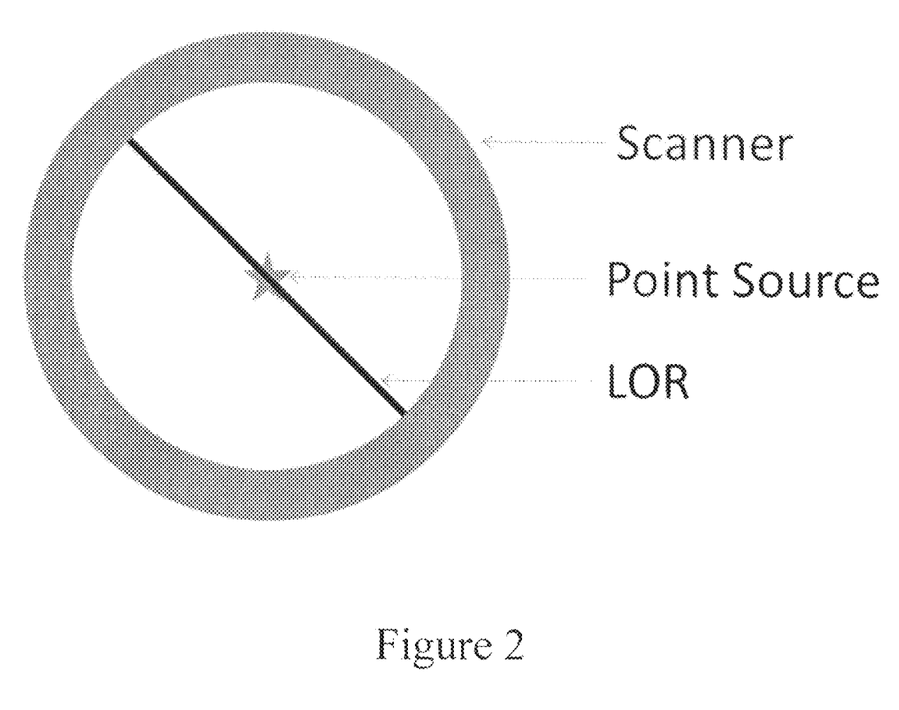
FIG. 2 illustrates a trans-axial view of a PET scanner and a single line-of-response (LOR)

Next, paired list-mode data is obtained from the list-mode data obtained from the scan. The paired list-mode data includes a list of the LORs, each corresponding to a detected annihilation event in which two gamma rays are detected by the scanner in diametrically opposite directions within a predetermined coincidence window. As noted above, the line joining the two detection positions (crystal locations) is called the LOR. FIG. 2 shows a transaxial view of a PET scanner and a single LOR.

The crystal positions are converted from crystal ID number(s) (using the knowledge of the scanner's fixed geometry) to Cartesian coordinates. Assume, for example, that A1, A2, A3, . . . AN represent LORs from the point source.

The two-dimensional (2D) intersection point between A1 and A2 is first calculated. The x Cartesian position of the intersection point is recorded and an x-histogram is generated, and the y position is recorded and a y-histogram is generated.

Figure 3:
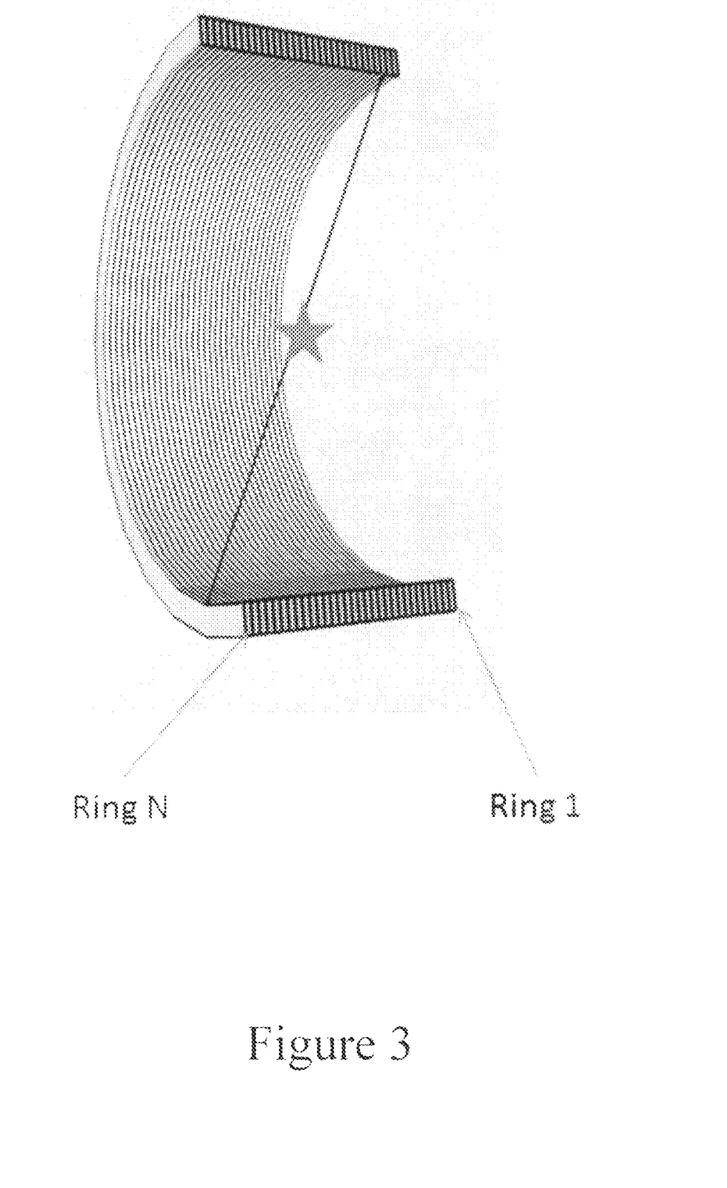
FIG. 3 illustrates an axial view of a PET scanner and a single LOR.

The crystal ID is also decoded to find out which ring the crystal corresponds to. For example, in FIG. 3, the LOR has ring positions 1 and N. The z position is calculated as the mean z position. Following the example illustrated in FIG. 3, the mean z position is (1+N)/2. Given the width of the ring (known from the scanner geometry), the z mean position can be converted to an axial position. This mean z position is recorded and a histogram z is generated.

Next, after calculating the x, y, and z intersection points from LORs A1 and A2, the same procedure is repeated for LORs A1 and A3, followed by A1 and A4, etc. for all LOR pairs in A1 to AN, where N is the last LOR.

After the aforementioned calculation, the intersection points for pairs (A2, A3), (A2, A4), (A2, A5), . . . (A2, AN), etc. are calculated. Accordingly, all possible pair permutations (without duplication) are used. For example, if there are 5 paired events: A, B, C, D, and E, then the following combinations shown in Table 1 below are possible:

TABLE 1

| A-B | B-C | C-D | D-E |
|-----|-----|-----|-----|
| A-C | B-D | C-E |     |
| A-D | B-E |     |     |
| A-E |     |     |     |

Figure 4A:
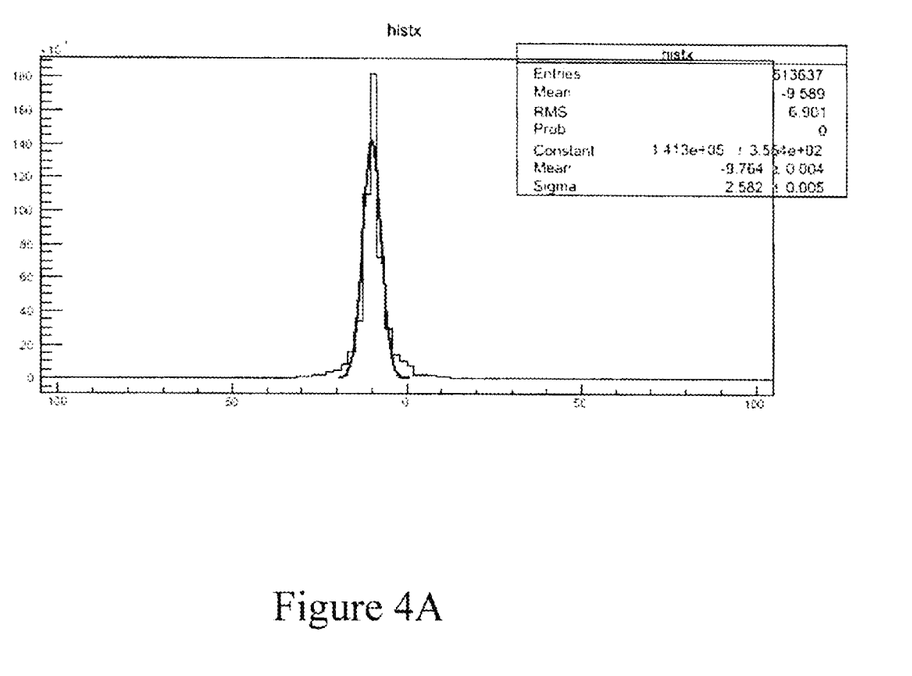
FIGS. 4A-4C illustrate histograms.
Figure 4B:
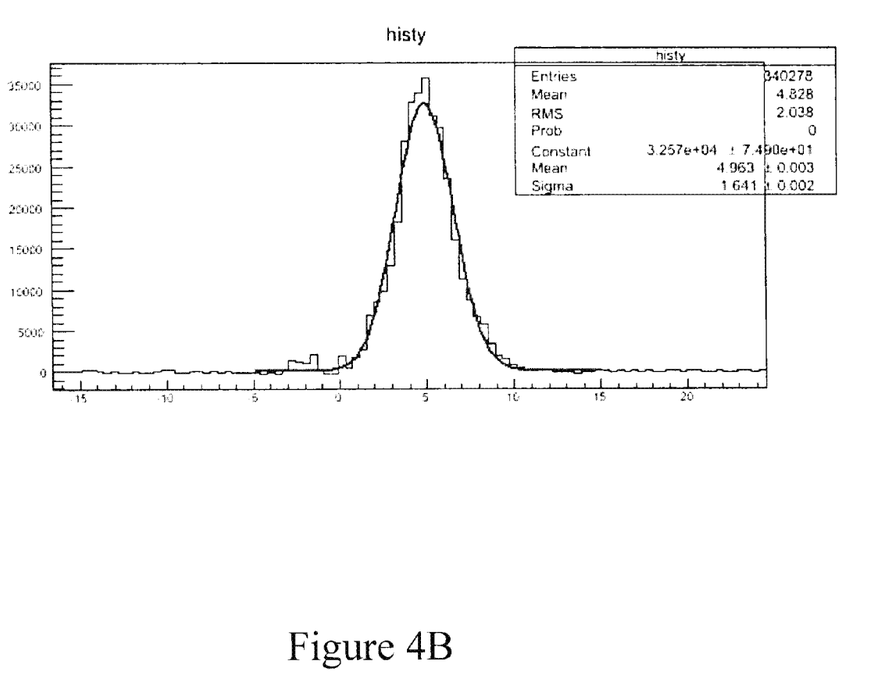
Figure 4C:
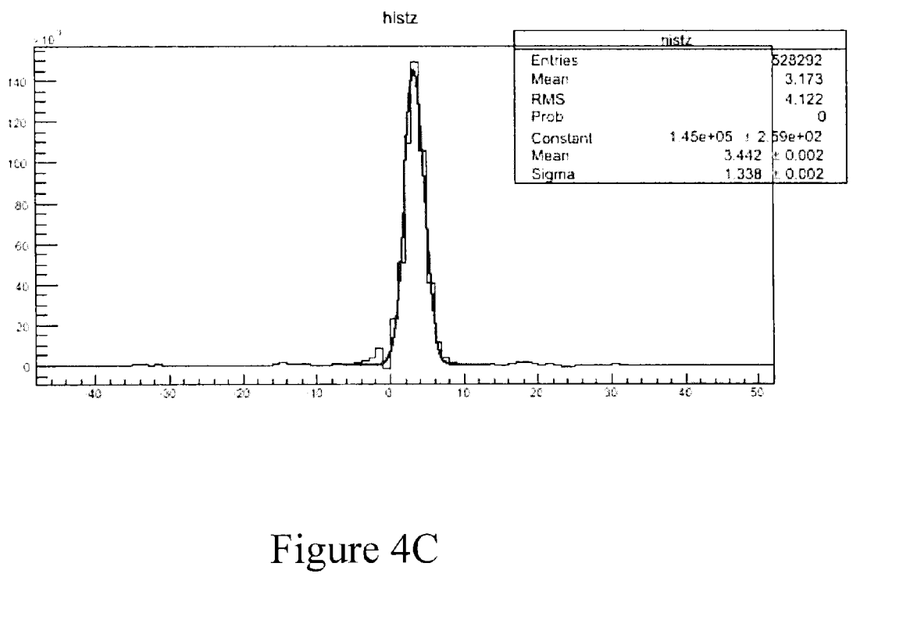

Next, a Gaussian-fit is performed for each of the sets of histogram data and the Gaussian center positions are indicative of the (x, y, z) location of the point source. For a simulated point source located at x=−10 mm, y=5 mm, and z=3 mm, the histograms for the x, y, and z positions are shown in FIGS. 4A, 4B, and 4C, respectively. FIGS. 4A-4C illustrate how the mean position of the fitted Gaussian is indicative of the point source position to within a fraction of millimeters.

As a result, the couch or patient bed can be iteratively moved to position the source at the exact center by moving the bed by the position indicated by the intersection points.

The embodiments below set forth the method discussed above in more detail.

As previously noted, one embodiment discussed herein describes the procedures and algorithms used in centering a radioactive point source at the iso-center of the PET scanner. A number of calibration procedures require the point source to be at the iso-center of the scanner, and for other procedures, the centering is desirable but not necessarily required. Setting the comparator thresholds is one example of a calibration requiring the point source at the iso-center. Some performance measurements also require the point source at the iso-center. For example, the published system performance of a scanner often sites the spatial resolution at the center in addition to the off-center.

In one embodiment, the method uses only a small number of PET paired events and is designed to provide a coarse position of the point source.

Figure 5:
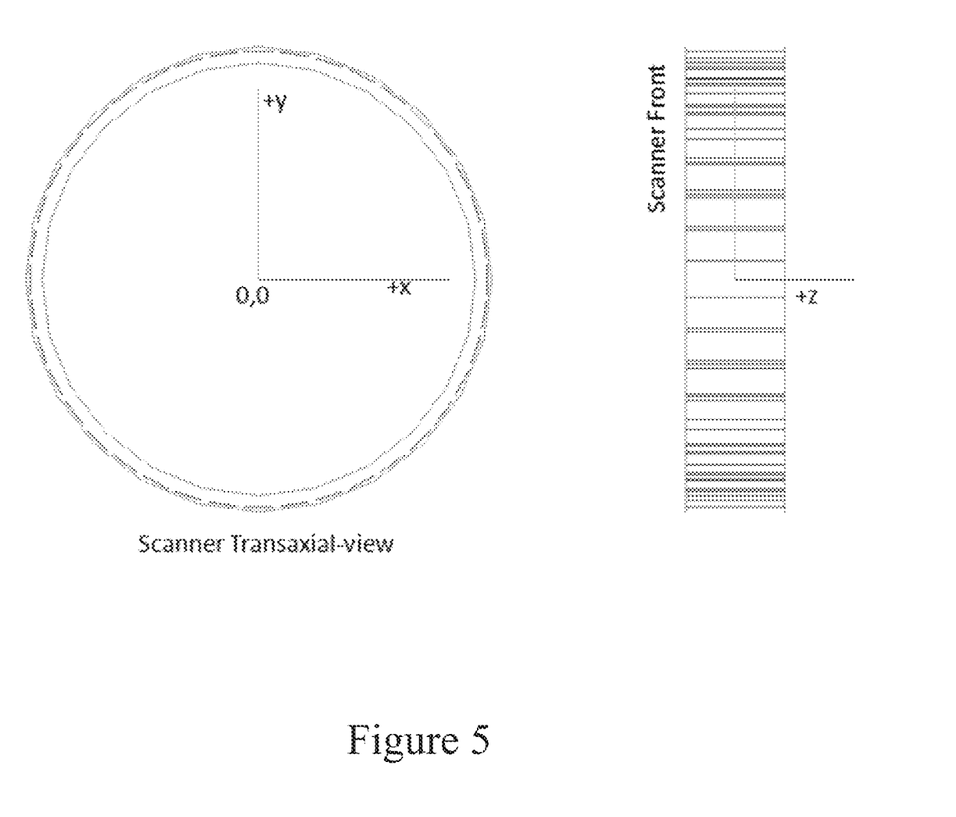
FIG. 5 illustrates the geometry of a PET scanner.

FIG. 5 illustrates the geometry of the PET scanner. The view of the scanner is shown from the front (patient table side) of the scanner. FIG. 5 further illustrates the positive x-axis, the positive y-axis, and the positive z-axis.

In one embodiment, the aforementioned method of positioning the source does not use any image data and is intended to serve as a fast method of estimating the source position. In one embodiment, the aforementioned method is performed before a calibration process. In one embodiment, the aforementioned method is performed as part of the calibration process.

In one embodiment, at least 5000 energy-qualified LORs are acquired. With a 1 mCi point source at the scanner iso-center, less than a second's worth of data acquisition provides enough data for the discussed coarse positioning process. In one embodiment, a different number of energy-qualified LORs can be acquired.

Figure 6:
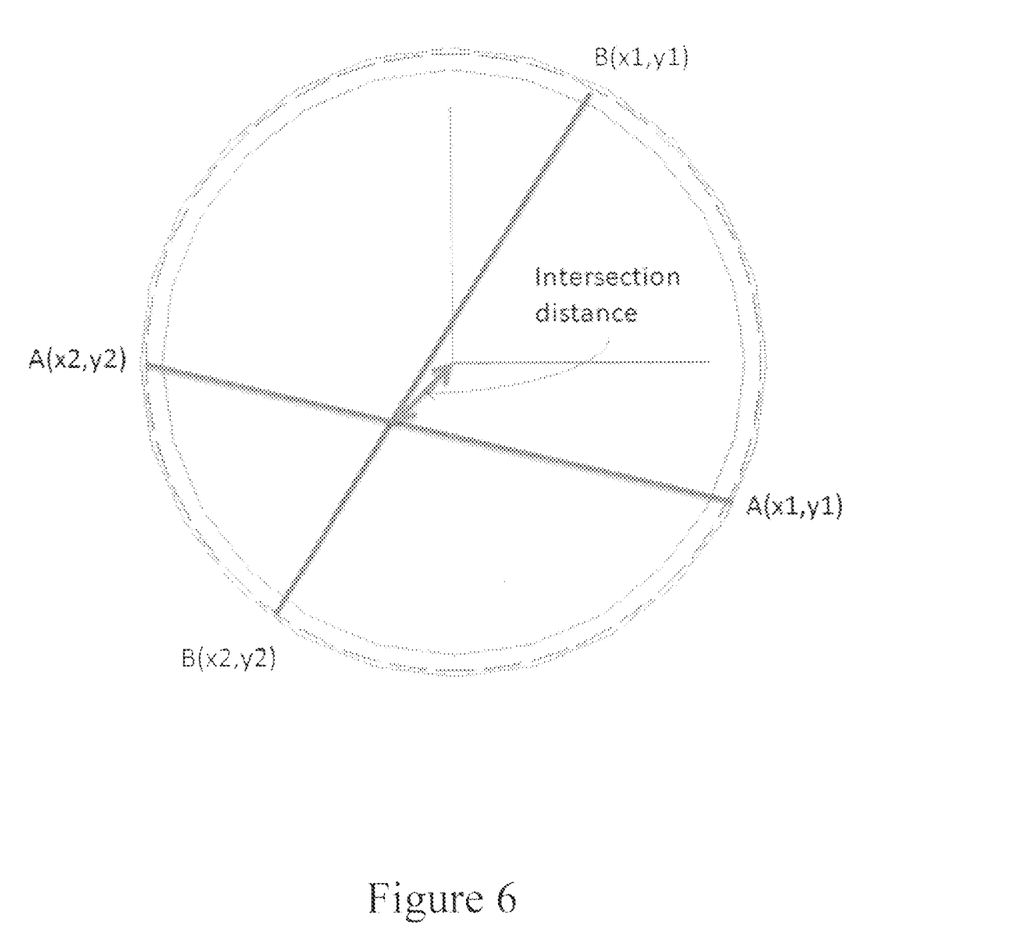
FIG. 6 illustrates two LORs.

FIG. 6 shows two events (event A and event B) giving rise to two LORs. In FIG. 6, event A is shown as a LOR with terminals at A(x1, y1) and A(x2, y2), and event B is shown as a LOR with terminals at B(x1, y1) and B(x2, y2). The intersection point between these two LORs is at an intersection distance from the scanner iso-center, as shown in FIG. 6.

In one method, the number of energy qualified list-mode events ('EventsToProcess') is specified by the user. "Energy qualified" events are those that have energy values as specified by the user.

The following process is performed to obtain (x1, y1, z1) for a first crystal in a LOR.

First, list-mode data is acquired with the point source positioned as close to the scanner iso-center as is possible by visual evaluation.

Second, the number EventsToProcess is read. Again, in one embodiment, the number EventsToProcess is set by the user. If omitted, the default value is 5000. In one embodiment, the events read will have an energy threshold also set by the user. The energy threshold is defined as one where the event is recorded if the energy of the gamma ray detected at crystal A and the energy of the gamma ray detected at crystal B in a LOR are both above the energy threshold. If the energy threshold is left undefined by the user, a default value of 400 keV is applied.

Third, for each qualified event read in the second step, the Cartesian coordinates of the crystal will be calculated.

Next, the z-position of the crystal is calculated from the axial crystal position using the axial crystal number of the LOR. Then, half a crystal size is subtracted to center the z position.

The above steps are repeated for the other (second) crystal in the LOR to obtain the location (x2, y2, and z2) of the crystal. The six (6) Cartesian coordinates x1, y1, z1, x2, y2, and z2 for each LOR are saved in an array.

Next, after the Cartesian coordinates have been calculated, the intersection point between two LORs (A and B) is calculated. The intersection point between each LOR and every other LOR is calculated using the method discussed above.

If the intersection point is within a predefined cylinder of radius point-source field-of-view (PSFOV), the intersection points x, y, z are histogrammed. PSFOV is a radius that is less than or equal to the scanner FOV. By default, PSFOV is set to an estimated number slightly greater than the error an operator can make when centering the sources in the trans-axial direction.

Next, histograms for the coordinates of the intersection points (for example, a one-dimensional histogram for each of x, y, and z) are generated and a Gaussian curve-fit is performed on the histograms. Note that the mean position of the Gaussian-fit is the calculated source position.

In one embodiment, a user or operator is informed of the source position in near real-time since the above-discussed method is very fast. Thus, the couch or patient table can be automatically moved in the z direction (axial, couch in/out) and y direction (vertical, couch up/down) in an iterative manner until the source is positioned in the axial and vertical positions.

In one embodiment, the user is informed to move the couch in the x direction (lateral direction, left/right) after the y-z centering. In one embodiment, after the user has completed this move in the x direction, the source position can be checked to determine whether it is within the specified tolerances.

In one embodiment, the couch can be automatically moved in the x direction (lateral direction, left/right) after the y-z centering using a computer-controlled motor driven system.

Figure 7:
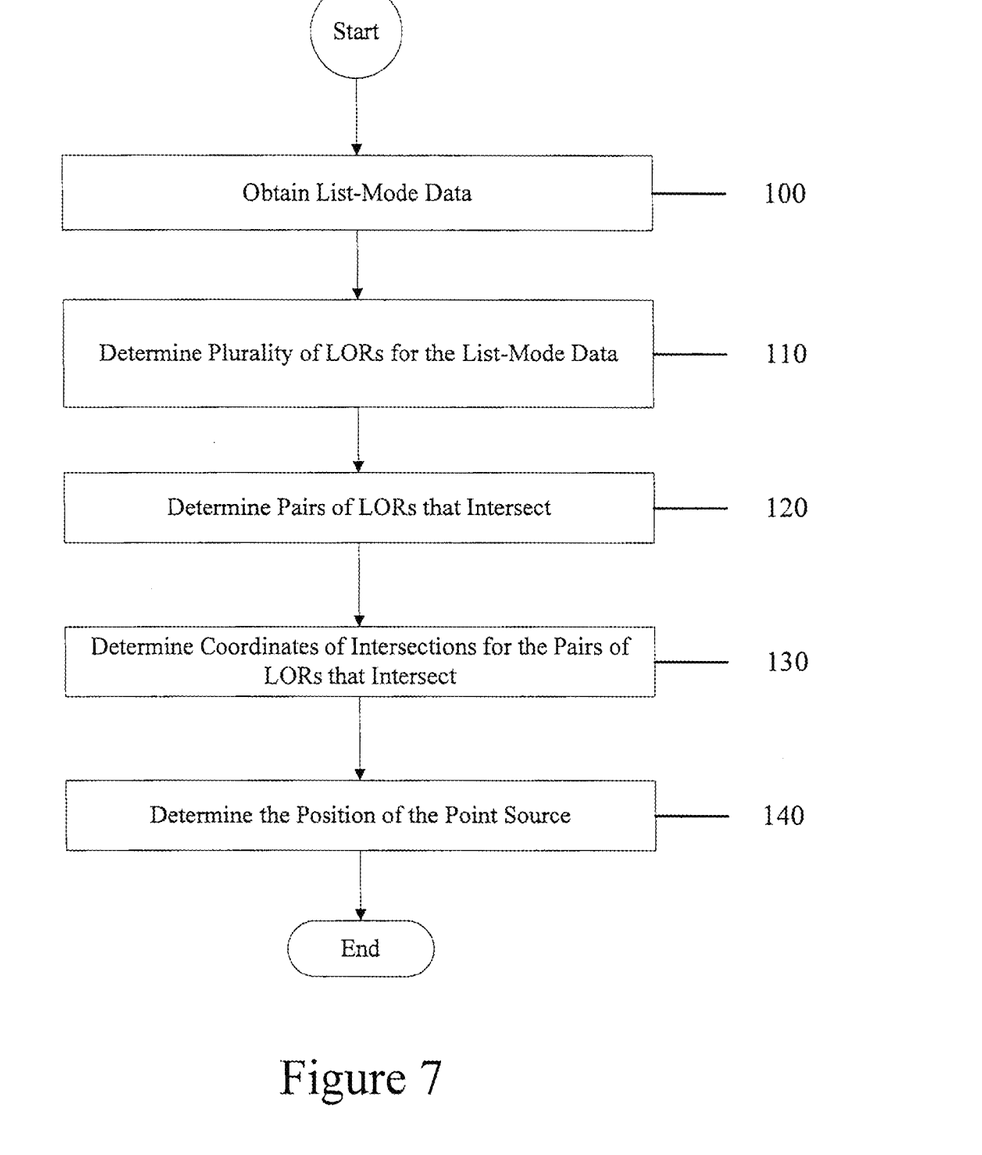
FIG. 7 illustrates a flowchart for determining the position of a point source.

FIG. 7 is a flowchart that summarizes the above-discussed process of determining the position of the point source. In step 100, list-mode data is obtained. Next, in step 110, a plurality of LORs is determined from the obtained list-mode data.

From the LORs determined in step 110, not all of the LORs will actually intersect. Thus, in step 120, the pairs of LORs (from the total LORs determined at step 110) that intersect are determined. Next, in step 130, the coordinates (x, y, z) of intersections for the pairs of LORs that intersect are determined. Finally, in step 140, the position of the point source is determined based on the coordinates of intersections determined in step 130.

Next, a method is discussed detailing the process of determining a position of a line source. For every annihilation point on the line, there are two detection points in the scanner ring (xa, ya, za) and (xb, yb, zb) that define the LORs. Data is collected for a few seconds yielding many (hundreds to millions) of LORs.

Irrespective of how the line source is oriented, for any annihilation point, the z-position of the interaction is computed by using the mean z value.

$$z = \frac{za + zb}{2}$$

First, three or more datasets are generated with the values shown in Table 2 below. Note that in Table 2, "a" is ¼ the scanner axial FOV.

TABLE 2

|  | Dataset 1 | Dataset 2 | Dataset 3 |
|---|---|---|---|
| Mean z-value | −a | 0 | +a |

Second, for each dataset, the (x, y) intersection point is calculated as discussed above for the point source. For each dataset m, there is a point in space (xm, ym, zm) where the line passes through. For example, for dataset 1, the point is given by (xm, ym, −a); for dataset 2, the point is given by (xm, ym, 0); and for dataset 3, the point is given by (xm, ym, +a).

Third, using the three (or more) points from the above step, a 3D orthogonal distance regression is performed to fit the data points to a line. Once the equation of the line is found, the tilt of the line with respect to the three axes is found by selecting any one point on the line, and estimating the direction cosines.

Figure 8:
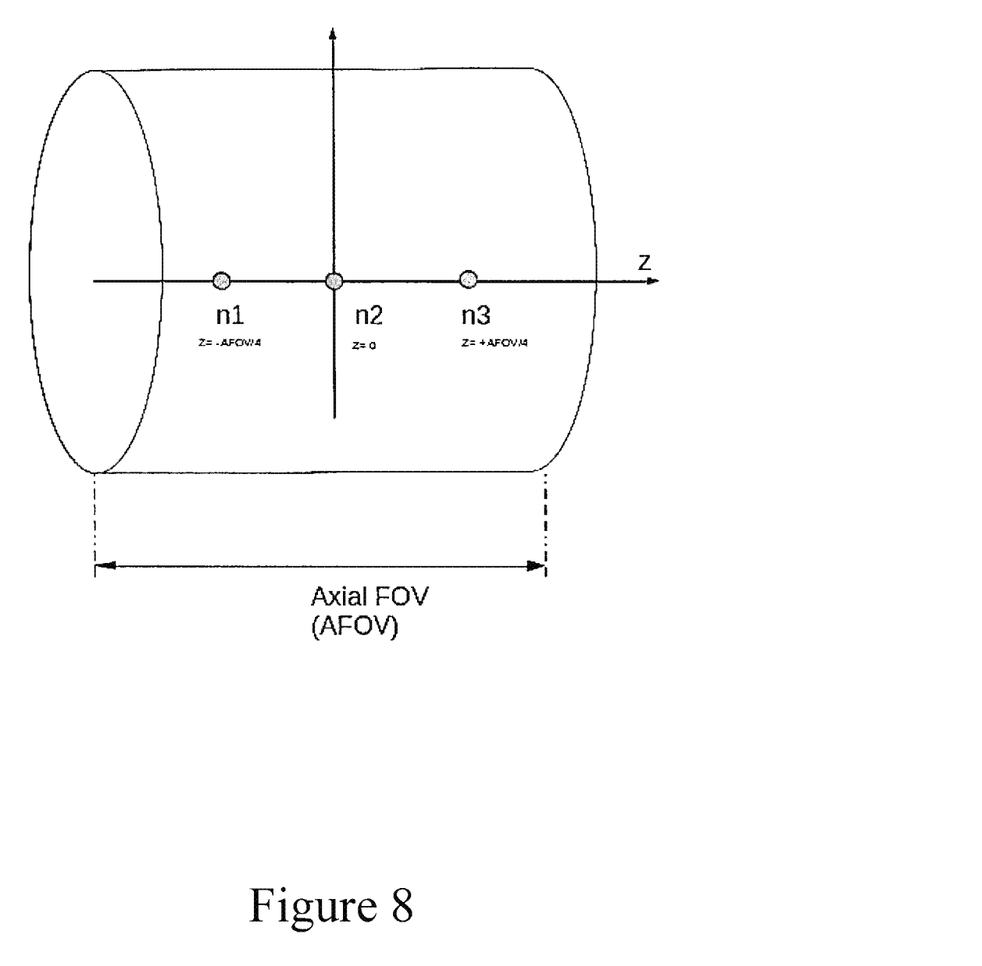
FIG. 8 illustrates points along the axial direction.

To briefly summarize the above-discussed process, FIG. 8 illustrates n points along the axial direction z. Note that n is equal to or greater than 3. For the first point, all LORs that have the following relationship are used:

$$n1 = \frac{z1 + z2}{2}$$

In the above case, z1 and z2 are the z positions of the LOR, and n1 is a fixed value. In following the example of FIG. 8, n1=−afov/4; n2=0; and n3=+afov/4.

Next, the (x, y) positions of the aforementioned n points are determined in the same way as performed with respect to the point source (discussed above). Finally, the position of the line source is determined by fitting a line that passes through the n points and determining the tilt of the line.

Figure 9:
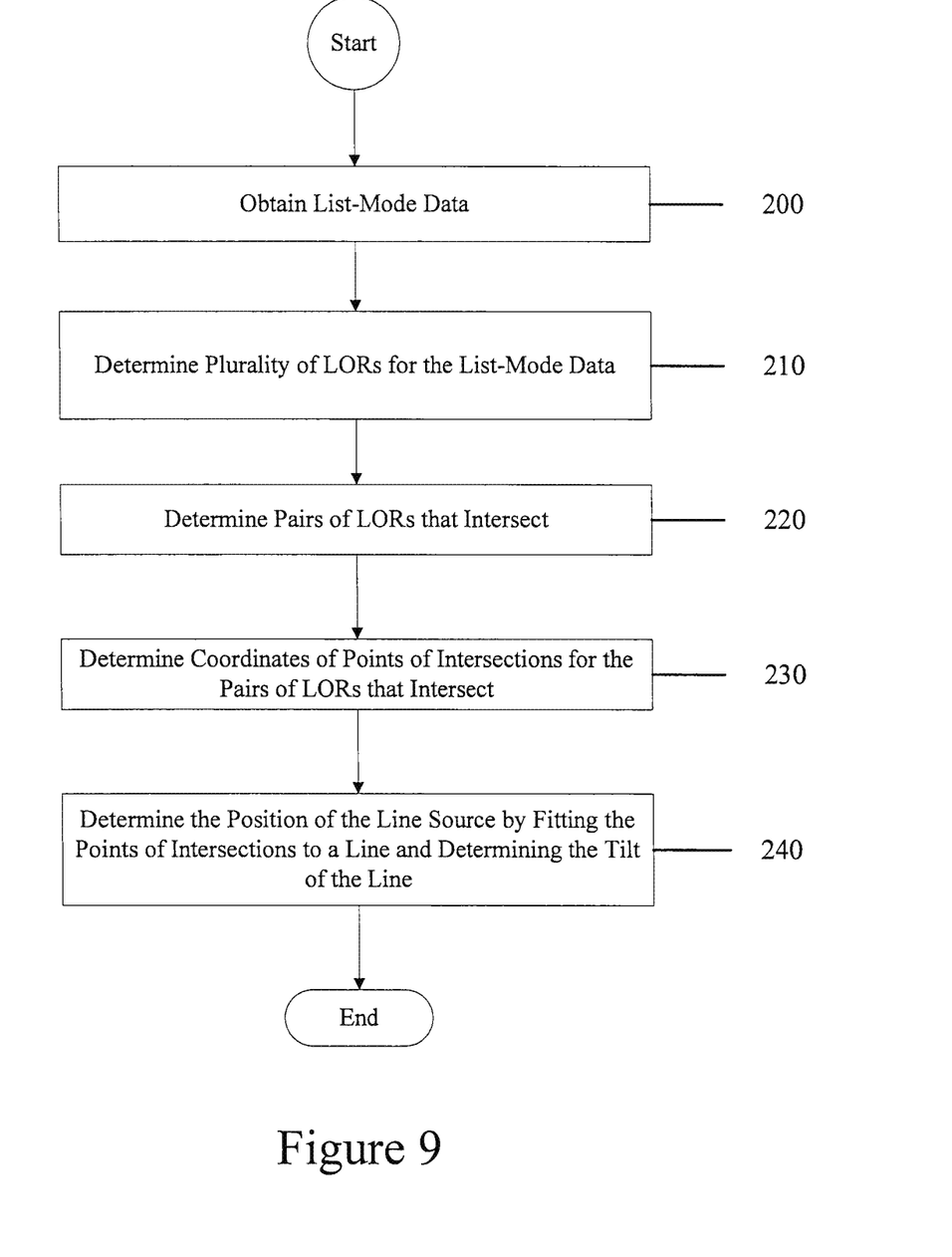
FIG. 9 illustrates a flowchart for determining the position of a line source.

FIG. 9 is a flowchart that summarizes the above-discussed process of determining the position of the line source. In step 200, list-mode data is obtained. Next, in step 210, a plurality of LORs is determined from the obtained list-mode data.

In step 220, the pairs of LORs (from the total LORs determined at step 210) that intersect are determined. Next, in step 230, the coordinates (x, y, z) of points of intersections for the pairs of LORs that intersect are determined. Finally, in step 240, the position of the line source is determined by fitting the points of intersections to a line and determining the tilt of the line.

Each of the functions/methods/processes described in the embodiments may be implemented by one or more processing circuits (or circuitry). A processing circuit includes a programmed processor (for example, processor 1203 of FIG. 10), as a processor includes circuitry. A processing circuit also includes devices such as an application specific integrated circuit (ASIC) and conventional circuit components arranged to perform the recited functions. The circuit/circuitry may be part of a PET scanner apparatus/system or may be a stand-alone apparatus/device/system that communicates with/controls the PET scanner apparatus/system.

Figure 10:
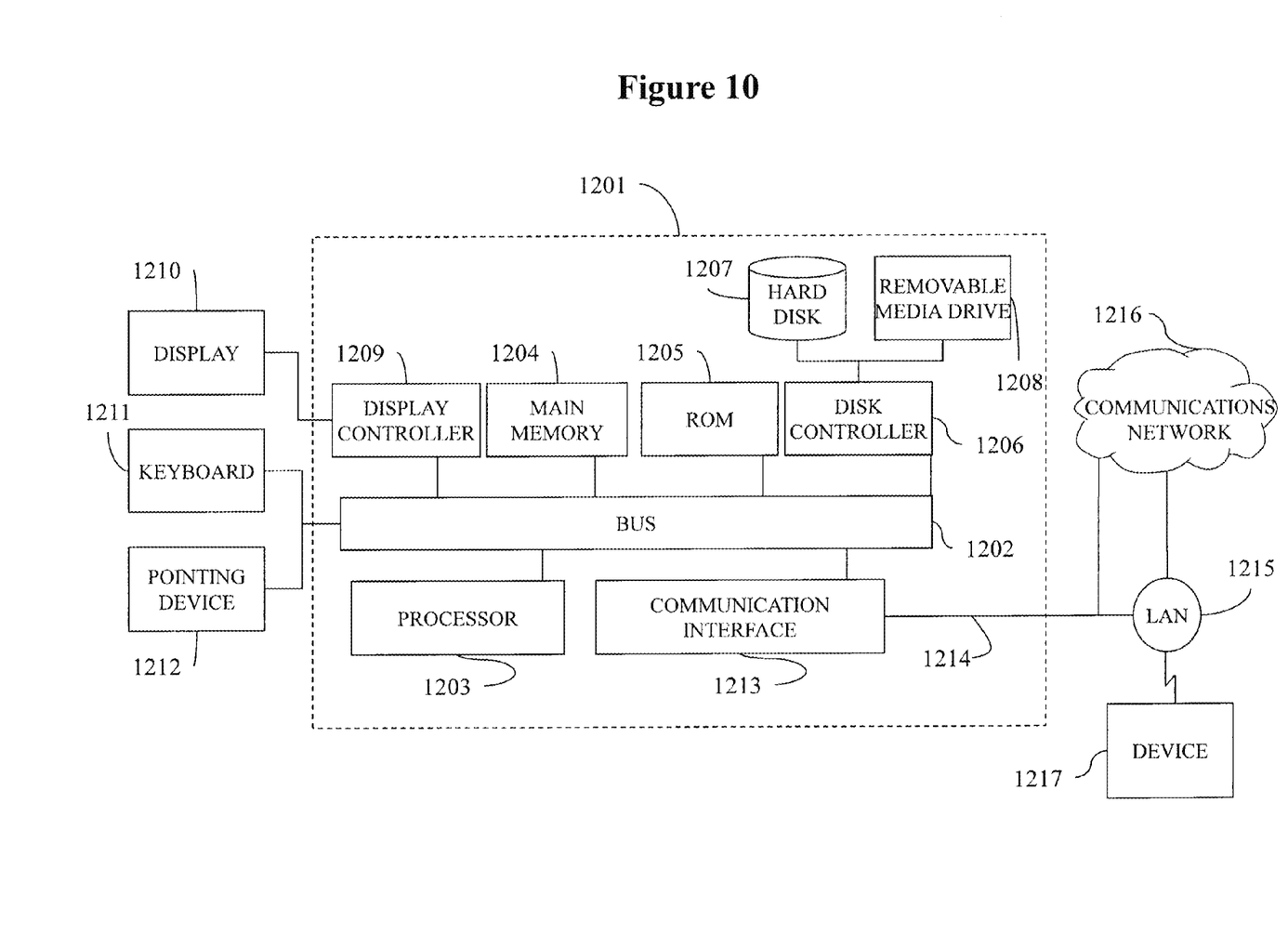
FIG. 10 illustrates a computer system upon which embodiment(s) of the present disclosure may be implemented.

Various components of the PET scanner apparatus/system or the stand-alone apparatus/device/system described above can be implemented using a computer system or programmable logic. FIG. 10 illustrates a computer system 1201 upon which embodiment(s) of the present disclosure may be implemented.

The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a liquid crystal display (LCD), for displaying information to a computer user. The computer system includes input devices, such as a keyboard 1211 and a pointing device 1212, for interacting with a computer user and providing information to the processor 1203. The pointing device 1212, for example, may be a mouse, a trackball, a finger for a touch screen sensor, or a pointing stick for communicating direction information and command selections to the processor 1203 and for controlling cursor movement on the display 1210.

The computer system 1201 performs a portion or all of the processing steps of the present disclosure in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A Positron Emission Tomography (PET) scanner apparatus comprising:
   a detector configured to detect a pair of gamma rays emitted from a point source; and
   processing circuitry configured to
      obtain list-mode data based on the pair of gamma rays detected by the detector,
      determine a plurality of lines-of-response (LORs) from the obtained list-mode data,
      determine intersecting pairs of LORs from the determined plurality of LORs,
      determine corresponding coordinates of intersection points of the determined intersecting pairs of LORs,
      determine the position of the point source based on the determined coordinates of the intersections points, and
      move a patient bed so that a position of the point source placed on the patient bed becomes a predetermined position for performing a calibration based on the determined position of the point source.

2. The PET scanner apparatus of claim 1, wherein the processing circuitry is configured to determine the position of the point source by generating histograms for the determined coordinates of the intersection points, and applying a Gaussian-fit to the histograms.

3. The PET scanner apparatus of claim 1, wherein the processing circuitry is further configured to perform a PET scan of the point source to obtain the list-mode data.

4. The PET scanner apparatus of claim 1, wherein the processing circuitry is further configured to cause the patient bed to move to the determined position of the point source.

5. The PET scanner apparatus of claim 1, wherein an intersection point between two LORs is at an intersection distance from iso-center of the PET scanner apparatus.

6. A method performed by a Positron Emission Tomography (PET) scanner apparatus comprising a detector and processing circuitry, the method comprising:
   detecting, by the detector, a pair of gamma rays emitted from a point source;
   obtaining list-mode data based on the pair of gamma rays detected by the detector;
   determining, by the processing circuitry, a plurality of lines-of-response (LORs) from the obtained list-mode data;
   determining, by the processing circuitry, intersecting pairs of LORs from the determined plurality of LORs;
   determining, by the processing circuitry, corresponding coordinates of intersection points of the determined intersecting pairs of LORs;
   determining, by the processing circuitry, the position of the point source based on the determined coordinates of the intersection points; and
   moving, by the processing circuitry, a patient bed so that the point source placed on the patient bed becomes a predetermined position for performing a calibration based on the determined position of the point source.

7. The method of claim 6, wherein the step of determining the position of the point source comprises determining the position of the point source by generating histograms for the determined coordinates of the intersection points, and applying a Gaussian-fit to the histograms.

8. The method of claim 6, further comprising:
   causing the PET scanner apparatus to perform the scan of the point source to obtain the list-mode data.

9. The method of claim 6, further comprising:
   causing the patient bed to move to the determined position of the point source.

10. A Positron Emission Tomography (PET) scanner apparatus comprising:
    a detector configured to detect a pair of gamma rays emitted from a line source; and
    processing circuitry configured to
       obtain list-mode data based on the pair of gamma rays detected by the detector,
       determine a plurality of lines-of-response (LORs) from the obtained list-mode data,
       determine intersecting pairs of LORs from the determined plurality of LORs,
       determine corresponding coordinates of points of intersections for the determined intersecting pairs of LORs,
       determine the position of the line source by fitting the points of intersections for the intersecting pairs of LORs to a line and determining tilt of the line, and
       move a patient bed so that a position of the line source placed on the patient bed becomes a predetermined position for performing a calibration based on the determined position of the line source.

11. The PET scanner apparatus of claim 10, wherein the processing circuitry is further configured to perform a PET scan of the line source to obtain the list-mode data.

12. The PET scanner apparatus of claim 10, wherein the processing circuitry is further configured to cause the patient bed to move to the determined position of the line source.

* * * * *